United States Patent [19]

Leonard

[11] Patent Number: 4,840,566

[45] Date of Patent: Jun. 20, 1989

[54] DEVICE FOR MAINTAINING A BORING TOOL IN A VIBRATORY DENTAL INSTRUMENT

[75] Inventor: Henri Leonard, Besancon, France

[73] Assignee: Micro-Mega, Besancon, France

[21] Appl. No.: 56,703

[22] Filed: Jun. 2, 1987

Related U.S. Application Data

[63] Continuation-in-part of Ser. No. 531,445, Sep. 12, 1983, Pat. No. 4,634,378.

[30] Foreign Application Priority Data

Jun. 2, 1986 [FR] France ................................ 86 08151

[51] Int. Cl.⁴ ............................................... A61C 1/14
[52] U.S. Cl. .................................... 433/127; 433/119; 433/102; 279/82
[58] Field of Search ........................ 433/102, 119, 127; 279/50, 82, 95

[56] References Cited

U.S. PATENT DOCUMENTS 4,484,891 11/1984 Nash ..................................... 433/127

FOREIGN PATENT DOCUMENTS 1097157 3/1954 France ................................... 279/82

Primary Examiner—Robert Peshock
Attorney, Agent, or Firm—Horst M. Kasper

[57] ABSTRACT

A tool holder is furnished for fastening a dentistry-type tool to be subjected to vibrations. A core is attached to a generator of vibrations and includes a housing for a tool. A locking assembly cap having a rear end is fitted onto a forward area of the core. A locking assembly sliding component is placed over a rear area of the core for contacting the rear end of the core with front end of the locking assembly cap. A compressive spring engages the core and the locking assembly sliding component for pushing the locking assembly sliding component in a forward direction.

19 Claims, 1 Drawing Sheet

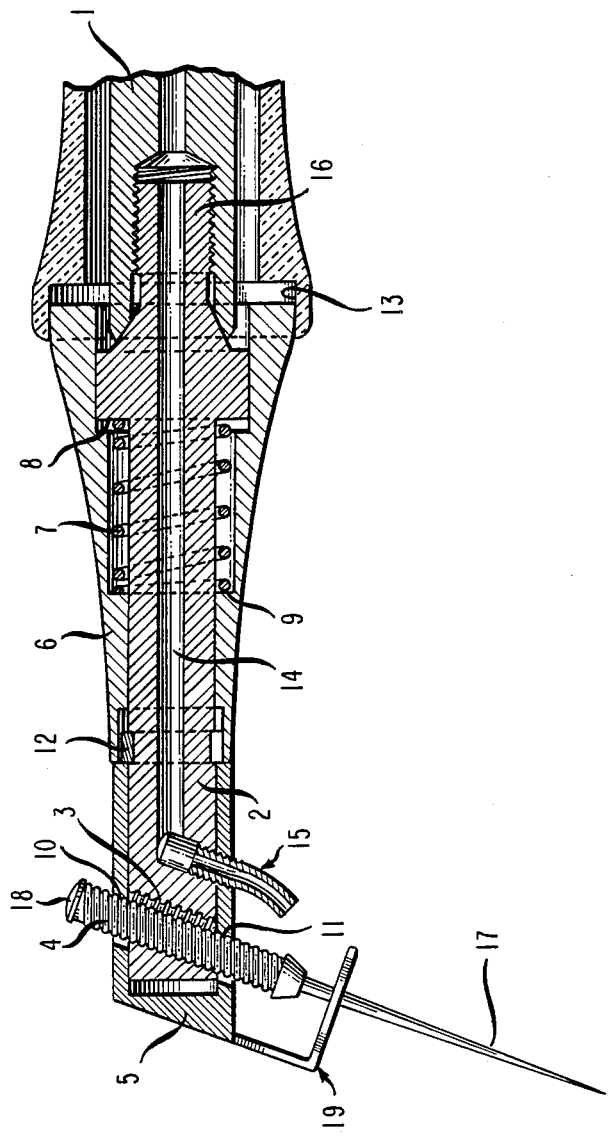

4,840,566

DEVICE FOR MAINTAINING A BORING TOOL IN A VIBRATORY DENTAL INSTRUMENT

CROSS-REFERENCE TO RELATED APPLICATIONS

This application is a continuation-in-part application of another application filed with the U.S. Patent and Trademark Office and bearing Ser. No. 531,445 filed Sept. 12, 1983 and now U.S. Pat. No. 4,634,378 issued Jan. 6, 1987. The entire disclosure of this latter application, including the drawings thereof, is hereby incorporated in this application as if fully set forth herein.

BACKGROUND OF THE INVENTION

1. Field of the Invention

The present invention relates to a device which which maintain a tool for boring the canals of teeth roots in a dental instrument which transmits vibratory movement to the boring tool.

2. Brief Description of the Background of the Invention Including Prior Art

A vibratory dental instrument of the type for which the instant maintaining device is intended has been described in U.S. Pat. No. 4,330,278.

French Pat. No. 2,535,198 discloses a device to maintain a boring tool in a vibratory dental instrument which includes a central tubular core with its near end linked to the vibratory movement so as to take up the vibration and its far end offset to form an elbow. The prolongation of its internal section is drilled out. The boring tool is positioned in the elbow and in the drilled out area and is maintained in position by a locking device screwed to the non-offset area of the core. The looking device exerts thrust on the two sides of the tool rod rising beyond the core.

The first certificate of addition to the above referenced French patent discloses that, when the tool is locked in its housing by the upper raised edge of the locking device screwed to the tool-holder, the locking device is itself maintained in position by a second locking device mounted behind it on the tool-holder and forming a nut/lock-nut assembly.

U.S. Pat. No. 4,580,979 is equivalent to French Pat. No. 82 18545 and its first certificate of addition as described above and provides a description in English of the above cited prior art.

Although the device as described above gives complete satisfaction, it is possible for the user to incorrectly tighten the locking device, which consequently is either too loose or too tight.

J. W. Ivory in U.S. Pat. No. 1,327,477 teaches a dental hand port polisher. Ivory shows a handle 2 with a bed 10 for seating a polishing piece apparently without means for proper tightening.

Scholz, Jr, in U.S. Pat. No. 4,229,168 teaches a contra-angle ultrasonic endodontic instrument. An endodontic tool may be received within a head 20 either at right angles to shaft 14 or at some substantial angle to shaft 14 apparently without a possibility for setting proper tightening.

SUMMARY OF THE INVENTION

1. Purposes of the Invention

It is an object of the present invention to provide an arrangement to eliminate the risk that the locking device will be incorrectly tightened and thus be too loose or too tight.

It is further object of the present invention to provide that the tool cannot slip out of the instrument, particularly when it is being released.

These and other objects and advantages of the present invention will become evident from the description which follows.

2. Brief Description of the Invention

According to the invention, a tool holder for fastening a dentistry-type tool to be subjected to vibrations comprises a core to be attached to a generator of vibrations and having a housing, a tool disposed in the housing, a locking assembly cap is fitted onto a forward area of the core and having a rear end, a locking assembly sliding component placed over a rear area of the core for contacting with a front end the rear end of the locking assembly cap, and a compressive spring engaging the core and the locking assembly sliding component for pushing the locking assembly sliding component in a forward direction.

A hole in a side of the locking assembly cap can be disposed neighboring to the housing of the core when the locking assembly cap is fitted onto the core. Preferably, two holes are disposed at opposite sides of the locking assembly cap such that each hole is disposed neighboring to the housing of the core when the locking assembly cap is fitted onto the core.

A circlip can be attached to the core and can provide a stop to the locking assembly sliding component for limiting the forward displacement of the locking assembly sliding component under the pressure of the compressive spring. An inner annular step can be included for surrounding the circlip with the inner cylinder of the step and for contacting the circlip with the annular face of the step. The spring is preferably disposed surrounding the core and inside of an inner rear step of the locking assembly sliding component. An inner channel can run through the bore for providing fluid to a drilling area. An outlet can be disposed in the core and connected to the inner channel running through the core for spraying fluid onto the drilling area. The tool can include a handle and a steel rod. The handle can be fitted into the housing and through holes of the locking assembly cap and is preferably maintained in position by a force of the spring. The handle into holes of the locking assembly cap and is preferably kept in position by form-locking maintained by a force of the spring. A depth gauge can be attached to the locking assembly cap. The housing can be grooved. The tool can have a handle to be placed in the housing, which handle is grooved for matching the form of the housing and for interlocking with sufficient play to enable the tool to be fitted or extracted while preventing any longitudinal displacement when locking or unlocking.

According to a second aspect of the invention, a tool holder is provided for fastening a dentistry-type tool, which toolholder is characterized in that the locking assembly is press fitted on the forward area of a core and is pushed forward locking a tool in position by a sliding component on the rear of the core, pressurized by a compressive spring itself pushing forwards.

A housing is preferably disposed in the core, which housing is grooved. The tool preferably has a handle to be placed in the housing, with handle is grooved for interlocking with sufficient play to enable the tool to be fitted or extracted while preventing any longitudinal displacement when locking or unlocking.

There is also provided a method for attaching a dentistry-type tool to be subjected to vibrations to a tool holder. A core having a housing is attached to a generator of vibrations. A compressive spring is placed over a rear area of the core for engaging the core. A locking assembly sliding component is slid over a rear area of the core such that the spring pushes the locking assembly sliding component in a forward direction. A locking assembly cap is slid onto a forward area of the core such that a forward end of the locking assembly sliding component engages a rear end of the locking assembly cap. A tool can be disposed in the housing for being supported by the housing and the locking assembly cap under the force of the compressive spring. A fluid can be passed through an inner channel running through the bore for spraying a drilling area.

According to the present invention, the locking assembly is adapted to the nose of the instrument not by screwing but by sliding in position to a pressurizing spring which bears upon the instrument and presses it at a constant force towards the locking device. The locking assembly is press-fitted on the forward area of the core and is pushed forward, locking the tool in position by a sliding component on the rear of the core, pressurized by a compressive spring itself pushing forwards. This ensures that the locking device is not adjusted too tightly or too loosely.

Further, in accordance with the invention, the tool column and its housing in the nose of the core form recessed and protruding components which interlock in the same manner as threading or grooving to prevent any axial displacement of the tool, thereby ensuring that the tool cannot slip out of the instrument even when being released. The housing of the tool and the column of the said tool are grooved, or similar, to interlock with sufficient play to enable the tool to be fitted or extracted while preventing any longitudinal displacement when locking or unlocking.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BREIF DESCRIPTION OF THE DRAWING

In the accordance drawing, in which is shown a possible embodiment of the present invention:

FIG. 1 is a longitudinal sectional schematic view of the device for maintaining a boring tool in a vibratory dental instrument which illustrates the locking device of the present invention.

DESCRIPTION OF INVENTION AND PREFERRED EMBODIMENT

According to FIG. 1, a threaded extension 16 of the hollow core 2 is screwed into a threaded socket in the vibration shaft 1 for example in the same manner as in the prior art referred to above. The area of the core 2 distant from the vibration shaft 1 contains a slanted housing 3 for the dental tool 4. the housing 3 can be a cylindrical or a frustro-conical hole in the core. The housing 3 is formed in the core 2 at an angle of from about 110 to 120 degrees with respect to the longitudinal axis of the core 2. The locking unit of tool 4 holding it in the housing is a cap 5, fitted to or slid over the end of the core 2 distant from the vibration shaft 1 and itself locked by an assembly 6 which, instead of being screwed to the core 2 as in the prior art, is also fitted onto or slid over the core 2 and is pushed toward the cap 5 by a spring 7, compressed between an outer ridge 8 of the fixed core 2 and an inner ridge 9 of the sliding assembly 6.

Preferably, the locking unit of tool 4 holding it in the housing is a cap 5, press fitted to the end of the core 2 distant from the vibration shaft 1 and itself locked by an assembly 6 which, instead of being screwed to the core 2 as in the prior art, is also press fitted onto the core 2 and is pushed toward the cap 5 by a spring 7, compressed between a ridge 8 of the fixed core 2 and a ridge 9 of the slid assembly 6.

Preferably, the locking unit of the tool 4 holding it in the housing is a cap 5, press fitted to the end of the core 2 distant from the vibration shaft 1 and itself locked by an assembly 6 which, instead of being screwed to the core 2 as in the prior art, is also press fitted onto the core 2 and is pushed toward the cap 5 by a spring 7, compressed between a ridge 8 of the fixed core 2 and a ridge 9 of the sliding assembly 6.

The end of the assembly 6 near to the vibration shaft 1 fits into a recess 13 of the vibration shaft 1.

Under the effect of the spring 7, assembly 6 pushes cap 5 forward, and raised edges 10 and 11 of the cap 5 maintain the tool 4 in its housing with an ever constant load since it is that of the spring 7, which is preferably formed from spring bronze or a steel spring.

The present invention further provides that the housing 3 is reamed or has circular grooves while the tool column 4 consists of sections fitting exacting into the reaming or grooves with a certain amount of play to facilitate fitting or removal of the tool.

When the tool 4 is fitted, it is held in place both by the fitting and by raised edges 10 and 11 of the cap. In order to release the tool, it is sufficient to slide assembly 6 toward the vibration shaft 1, thus compressing the spring 7. The tool is then released and, because of the play between the aforementioned threading or grooving, it is possible to extract the tool without risk of its escaping by sliding free of its housing 3.

A circlip 12 limits the travel of assembly 6 in the direction of the end of the core 2 distant from the vibration shaft under the effect of spring 7. The positioning of the circlip 12 thus assures that the pressure exerted by assembly 6 on the cap 5 is sufficient to hold the raised edges 10 and 11 of the cap 5 firmly against the tool 4 but not so tightly that the tool undergoes excessive force. The strength of the spring 7 is also to be chosen to provide the desired pressure to hold the tool 4 firmly in place.

A depth gauge 19 can be attached to the cap 5 for maintaining a position of the boring tool relative to a boring area.

The hollow portion 14 of the core 2 serves as a fluid channel to provide irrigating and/or cooling fluid to the drilling area or to a bore hole, generated for example by spraying. The hollow portion 14 is connected to an outlet 15 as is usual with conventional dental drilling instruments.

The dental tool 4 can be of but is not limited to differing conventional types such as files, broaches, scrapers, rasps and more generally, any canal instrument havint a drilling function. In the context of the present invention the tool 4 is to be provided at its column end fitting into the housing 3 with grooves or reaming fitting into the grooves or reaming of the housing 3. The tool 14 is generally a reamer including a steel and preferably stainless steel rod 17 fixedly attached to a handle 18. In general, the handle can be made of a plastic material, preferably a synthetic polymeric organic material. Alternatively, the handle 18 can be of metal. The steel rod 17 can carry barbs, whiskers, grooves, channels, flutes, which are preferably helically disposed around the steel rod 17. Such tools 4 are disposed for example in U.S. Patent applications Ser. No. 01/531,445 and Ser. No. 06/799,359, which are included in this disclosure by reference.

It will be understood that each of the elements described above, or two or more together, may also find a useful application in other types of tool attachment and position maintenance procedures differing from the type described above.

While the invention has been illustrated and described as embodied in the context of a device for maintaining a dental tool in a vibratory dental instrument, it is not intended to be limited to the details shown, since various modifications and structural changes may be made without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by LETTERS Patent is set forth in the appended claims.

1. A tool holder for fastening a dentistry-type tool to be subjected to vibrations comprising a core to be attached to a generator of vibrations and having a housing;
   a locking assembly cap is fitted onto a forward area of the core and having a rear end;
   a tool to be subjected to vibrations supported in the forward area of the core and locked in position by the locking assembly cap;
   a circlip attached to the core of a position following the locking assembly cap;
   a locking assembly sliding component placed over a rear area of the core for contacting with a front end the rear end of the locking assembly cap and said circlip providing a stop to the locking assembly sliding component; and
   a compressive spring component engaging the core and the locking assembly sliding component for pushing the locking assembly sliding component in a forward direction whereby the forward displacement of the locking assembly sliding component under the pressure of the compressive spring is limited based on the presence of the circlip.

2. The tool holder for fastening a dentistry-type tool to be subjected to vibrations according to claim 1 further comprising
   a hole in a side of the locking assembly cap disposed neighboring to the housing of the core when the locking assembly cap is fitted onto the core.

3. The tool for fastening a dentistry-type tool to be subjected to vibrations according to claim 1 further comprising
   two holes disposed at opposite sides of the locking assembly cap such that each hole is disposed neighboring to the housing of the core when the locking assembly cap is fitted onto the core.

4. <The> A tool holder for fastening a dentistry-type tool to be subjected to vibrations <according to claim 1 further> comprising
   a core to be attached to a generator of vibrations and having a housing;
   a locking assembly cap is fitted onto a forward area of the core and having a rear end;
   a tool to be subjected to vibrations supported in the forward area of the core and locked in position by the locking assembly cap;
   a locking assembly sliding component placed over a rear area of the core for contacting with a front end the rear end of the locking assembly cap;
   a circlip attached to the core and below the locking assembly sliding compontent near a rear end of the locking assembly cap and providing a stop to the locking assembly sliding compontent; and
   a compressive spring engaging the core and the locking assembly sliding component for pushing the locking assembly sliding component in a forward direction, wherein the circlip limits <for limiting> the forward displacement of the locking assembly sliding component under the pressure of the compressive spring.

5. The tool holder for fastening a dentistry-type tool to be subjected to vibrations according to claim 1 wherein the locking assembly sliding component comprises an inner annular step for surrounding the circlip with the inner cylinder of the step and for contacting the circlip with the annular face of the step.

6. The tool holder for fastening a dentistry-type tool to be subjected to vibrations according to claim 1 wherein the spring is disposed surrounding the core and inside of an inner rear step of the locking assembly sliding component.

7. The tool holder for fastening a dentistry-type tool to be subjected to vibrations according to claim 1 further comprising an inner running through the bore for providing fluid to a drilling area.

8. The tool holder for fastening a dentistry-type tool to be subjected to vibrations according to claim 7 further comprising
   an outlet disposed in the core and connected to the inner channel running through the core for spraying fluid onto the drilling area.

9. The tool holder for fastening a dentistry-type tool to be subjected to vibrations according to claim 1 wherein the tool includes a handle and a steel rod.

10. The tool holder for fastening a dentistry-type tool to be subjected to vibrations according to claim 9 wherein the handle is fitted into the housing and through holes of the locking assembly cap and is maintained in position by a force of the spring.

11. The tool holder for fastening a dentistry-type tool to be subjected to vibrations according to claim 9 wherein the handle is formed to be lockingly fitted into the housing and into holes of the locking assembly cap and is kept in position by form-locking maintained by a force of the spring.

12. The tool holder for fastening a dentistry-type tool to be subjected to vibrations according to claim 1 further comprising
   a depth gauge attached to the locking assembly cap.

13. The tool holder for fastening a dentistry-type tool to be subjected to vibrations according to claim 1 wherein the housing is grooved and wherein the tool has a handle to be placed in the housing, which handle is grooved for matching the form of the housing and for interlocking with sufficient play to enable the tool to be fitted or extracted while preventing any longitudinal displacement when locking or unlocking.

14. The tool holder for fastening a dentistry-type tool to be subjected to vibrations according to claim 4 wherein the locking assembly sliding component comprises an inner annular step for surrounding the circlip with the inner cylinder of the step and for contacting the circlip with the annular face of the step.

15. A tool holder for fastening a dentistry-type tool characterized in that the locking assembly is press fitted on the forward area of a core and is pushed forward locking a tool in position by a sliding component on the rear of the core, pressurized by a compressive spring itself pushing forwards.

16. The tool holder for fastening a dentistry-type tool according to claim 15 wherein a housing disposed in the core is grooved and wherein the tool has a handle to be placed in the housing, which handle is grooved for interlocking with sufficient play to enable the tool to be fitted or extracted while preventing any longitudinal displacement when locking or unlocking.

17. A method for fastening a dentistry-type tool to be subjected to vibrations to a tool holder comprising attaching a core having a housing to a generator of vibrations;

placing a compressive spring over a rear of the core for engaging the core and a locking assembly sliding component;

attaching a circlip to the core and providing a stop to the locking assembly sliding component for limiting the forward displacement of the locking assembly sliding component under the pressure of the compressive spring;

sliding the locking assembly sliding component over a rear area of the core such that the spring pushes the locking assembly sliding component in a forward direction;

sliding a locking assembly cap onto a forward area of the core such that a forward end of the locking assembly sliding component engages a rear end of the locking assembly cap; and supporting a tool to be subjected to vibrations in the housing for being supported by the housing at the core and locking the tool with the locking assembly cap under the force of the compressive spring.

18. The method for fastening a dentistry-type tool to be subjected to vibrations to a tool holder according to claim 17 further comprising passing fluid through an inner channel running through the bore for spraying a drilling area.

19. The method for fastening a dentistry-type tool to a tool holder according to claim 17 further comprising surrounding the circlip with the inner cylinder of an inner annular step of the locking assembly sliding component; and contacting the circlip with an annular face of the step.

* * * * *